(12) United States Patent
Mathew

(10) Patent No.: US 10,770,173 B2
(45) Date of Patent: Sep. 8, 2020

(54) EFFECTING PAYMENTS USING OPTICAL COUPLING

(71) Applicant: Apple Inc., Cupertino, CA (US)

(72) Inventor: Binu K. Mathew, Los Gatos, CA (US)

(73) Assignee: APPLE INC., Cupertino, CA (US)

( * ) Notice: Subject to any disclaimer, the term of this patent is extended or adjusted under 35 U.S.C. 154(b) by 1002 days.

(21) Appl. No.: 15/240,588

(22) Filed: Aug. 18, 2016

(65) Prior Publication Data
US 2016/0357938 A1 Dec. 8, 2016

Related U.S. Application Data

(62) Division of application No. 13/481,916, filed on May 28, 2012, now abandoned.

(51) Int. Cl.
| | |
|---|---|
| *G16H 20/10* | (2018.01) |
| *G06Q 20/32* | (2012.01) |
| *G06Q 20/02* | (2012.01) |
| *G06Q 20/10* | (2012.01) |
| *G06Q 30/02* | (2012.01) |
| *G06F 19/00* | (2018.01) |

(52) U.S. Cl.
CPC ........... *G16H 20/10* (2018.01); *G06F 19/328* (2013.01); *G06Q 20/023* (2013.01); *G06Q 20/102* (2013.01); *G06Q 20/3276* (2013.01); *G06Q 30/02* (2013.01)

(58) Field of Classification Search
CPC ... G06F 19/3456; G06F 19/328; G06Q 30/02; G06Q 20/3223; G06Q 20/3276; G06Q 20/102; G06Q 20/023
See application file for complete search history.

(56) References Cited

U.S. PATENT DOCUMENTS

| | | | |
|---|---|---|---|
| 6,892,941 B2 * | 5/2005 | Rosenblum | G06F 19/3462 235/383 |
| 7,426,475 B1 * | 9/2008 | Tangellapally | G16H 10/60 705/3 |

(Continued)

FOREIGN PATENT DOCUMENTS

| | | |
|---|---|---|
| WO | 2009/100488 | 8/2009 |
| WO | 2012/097310 | 7/2012 |

OTHER PUBLICATIONS

Gao et al., "A 2D Barcode-Based Mobile Payment System," Third International Conference on Multimedia and Ubiquitous Engineering, 2009. MUE '09. Date of Conference: Jun. 4-6, 2009, pp. 320-329.

*Primary Examiner* — Eliza A Lam
(74) *Attorney, Agent, or Firm* — Polsinelli LLP

(57) ABSTRACT

The present technology relates to secure mobile payment systems for interacting with traditional paper invoices. Generating optical codes in a clearinghouse which, when decoded by a customer device, provides the customer with an anonymous portal for reconciling an invoice through the clearinghouse. Effecting payments by utilizing mobile devices equipped with digital camera, software for decoding optical codes, and an infrastructure of network-based clearinghouses for maintaining the anonymity of a plurality of customers and protecting their private and financial data. The present technology relates to a prescription lifecycle management system using optical coupling.

18 Claims, 11 Drawing Sheets

(56) References Cited

U.S. PATENT DOCUMENTS

| | | | |
|---|---|---|---|
| 8,626,530 B1* | 1/2014 | Tran | G06Q 50/22 |
| | | | 705/2 |
| 8,714,439 B2 | 5/2014 | Brendell et al. | |
| 9,659,284 B1* | 5/2017 | Wilson | G06K 7/10722 |
| 10,089,606 B2* | 10/2018 | Ihm | G06Q 20/02 |
| 2008/0228642 A1 | 9/2008 | Kim et al. | |
| 2011/0153398 A1 | 6/2011 | Tjhai et al. | |
| 2011/0191149 A1 | 8/2011 | Blackhurst et al. | |
| 2011/0270751 A1 | 11/2011 | Csinger et al. | |
| 2012/0084162 A1 | 4/2012 | Smith et al. | |
| 2012/0130888 A1* | 5/2012 | Cooke | G06Q 20/3272 |
| | | | 705/39 |
| 2012/0290422 A1 | 11/2012 | Bhinder | |

* cited by examiner

EFFECTING PAYMENTS USING OPTICAL COUPLING

CROSS-REFERENCE TO RELATED APPLICATIONS

This application is a divisional of U.S. Non-Provisional patent application Ser. No. 13/481,916, entitled "EFFECTING PAYMENTS USING OPTICAL COUPLING" and filed May 28, 2012, the contents of which are hereby incorporated by reference in their entirety as if fully set forth herein.

BACKGROUND

1. Technical Field

The present technology relates generally to systems and methods for carrying out secure transactions. More specifically, the present technology relates to systems and methods for performing secure transactions using optical codes and optical code readers.

2. Introduction

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Many payment instruments currently exist and may be used to carry out a financial transaction between two or more parties. For example, payments may be made using cash, credit cards, debit cards, checks, electronic checks, and so forth. In recent years, the growth of electronic commerce may be at least partially attributed to the popularity of credit cards, debit cards, and other hard non-currency based payment instruments. Thus, while merchants generally continue to accept cash and other hard currency as a method of payment for goods and/or services, most merchants now also accept payments made using credit cards, debit cards, stored-value (e.g., pre-paid) cards, checks, and electronic checks. In particular, online merchants (e.g., those operating "virtual stores" on the Internet or World Wide Web) may rely heavily on the use of credit and debit cards.

Mobile devices, such as personal digital assistants and Smartphones, have become increasingly ubiquitous in our society. Indeed, attempts have been made to extend the functionality of these devices to carry out financial transactions. However, these attempts often require either a wired connection with a merchant (e.g., online wallets) or an electro-magnetic coupling with a designated reader (e.g., Bluetooth, Near Field Communication). Unfortunately, these types of mobile payment systems are vulnerable to privacy breaches and cannot interact with traditional paper bills and invoices. Accordingly, it is desirable to extend the benefits of a mobile payment system to situations involving traditional paper bills, invoices, prescriptions, etc. and also to ensure the privacy of the users of these novel systems.

SUMMARY

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by practice of the principles set forth herein.

In view of the concerns now recognized and stated above, some embodiments of the present technology preserve the anonymous aspects of cash transactions while performing electronic transactions by utilizing optical codes that link a client device with a clearinghouse that anonymizes the transaction. Some embodiments involve a clearinghouse establishing an account with a merchant, receiving merchant invoices along with a claim number, associating the invoice with the claim number, storing the invoice on a server, and encoding the claim number as an optical code. When the optical code is presented to a customer, the customer's device decodes the optical code, retrieves the invoice from the server using the claim number as a reference, and is presented with an interface for authorizing payment for the invoice in the clearinghouse. The clearinghouse then sends the merchant a confirmation that the invoice was paid; however, the clearinghouse does not give the merchant any information about the customer.

In some embodiments of the present technology, one or more parties to a transaction utilize mobile devices equipped with digital camera and software for decoding optical codes. For example, some embodiments of the present technology involve generating invoices containing Quick Response codes ("QR codes") and decoding the QR codes using a camera and QR recognition software.

Some embodiments of the present technology, involve an infrastructure of network-based clearinghouses for maintaining the anonymity of a plurality of customers and protecting their private and financial data. According to some embodiments, both merchants and customers maintain verified accounts with one or more clearinghouses. Similarly, some embodiments of the present technology involve methods for maintaining the anonymity of a plurality of customers and protecting their private and financial data. In some embodiments, transaction data is separated into core data and auxiliary data to further protect sensitive information.

Some embodiments of the present technology are particularly useful in scenarios involving multiple customers dividing a single invoice. According to these embodiments, the clearinghouse records individual contribution, provides updated invoices to customers as parts of an invoice are reconciled, and presenting a record of a fully reconciled invoice to the merchant.

Some embodiments of the present technology involve using optical codes in a variety of scenarios involving the transfer of sensitive information. For example, some embodiments of the present technology extend optical coupling to the medical field where prescription drug transcription errors are extremely dangerous and can be made very easily. Some embodiments involve clearinghouses being used to associate a claim number with a prescription, receive prescriptions generated by a medical professional, store the prescriptions using the claim number as a reference, and encode the claim number in an optical code. The optical code is transferred to a pharmacist whose device decodes the claim number, retrieves the prescription using the claim number, and is presented with the prescription information. Some embodiments can also involve notifying the prescribing doctor that the prescription was filled. Some embodiments can also involve the clearinghouse managing prescription refills.

This brief summary has been provided so that the nature of the technology may be understood quickly. A more complete understanding of the technology can be obtained by reference to the following descriptions of the preferred embodiments thereof in connection with the drawings, which together form a complete specification.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

Figure 1:
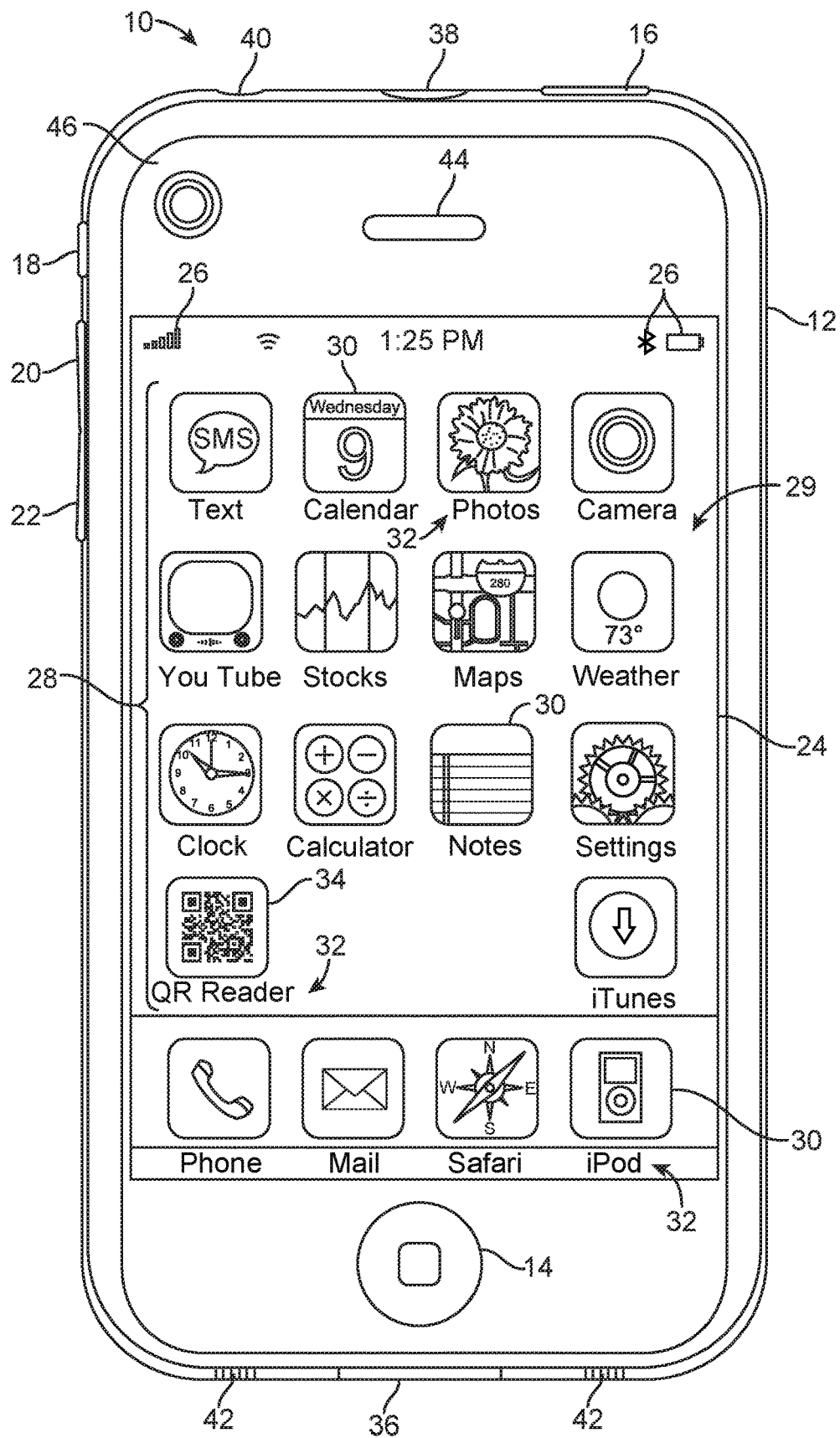
FIG. 1 is a front view of an electronic device in accordance with some embodiments of present technology.

The present disclosure addresses the need in the art for mobile payment systems that are not vulnerable to privacy breaches and that can interact with traditional paper bills or invoices. Some embodiments of the present technology involve merchants generating optical codes in a clearinghouse which, when decoded by a customer device, provides the customer with a portal for reconciling an invoice through the clearinghouse. According to these embodiments, the customer maintains anonymity from the merchant because the customer never reveals personal or financial information to the merchant. Also, the merchant can be notified that the invoice has been fully satisfied. In some embodiments of the present technology, the parties to a transaction utilize mobile devices equipped with digital camera and software for decoding optical codes. FIG. 1 illustrates a mobile device equipped with a camera according to some embodiments of the present technology.

According to FIG. 1, a handheld processor-based electronic device that may comprise a camera for issuing invoices and/or processing payments in accordance with the techniques briefly described above is illustrated and generally referred to by reference numeral 10. While the techniques will be described below in reference to the illustrated handheld electronic device 10 (which may be a cellular telephone, a media player for playing music and/or video, a personal data organizer, or any combination thereof), it should be understood that the techniques described herein may be implemented using any type of suitable electronic device, including non-portable electronic devices, such as a desktop computer or a workstation.

As illustrated in FIG. 1, the electronic device 10 may be a handheld device incorporating the functionality of one or more portable devices, such as a media player, a cellular phone, a personal data organizer, and so forth. Thus, depending on the functionalities provided by the electronic device 10, a user may listen to music, play games, record video, take pictures, and place telephone calls, while moving freely with the device 10. In addition, the electronic device 10 may allow a user to connect to and communicate through the Internet or through other networks, such as local or wide area networks. For example, the electronic device 10 may allow a user to communicate using e-mail, text messaging, instant messaging, or other forms of electronic communication. The electronic device 10 also may communicate with other devices using short-range connection protocols, such as Bluetooth and near field communication (NFC). By way of example only, the electronic device 10 may be a model of a MacBook®, iPod®, iPad®, or an iPhone®, available from Apple Inc. of Cupertino, Calif.

In the depicted embodiment, the device 10 includes an enclosure 12 that protects the interior components from physical damage and shields them from electromagnetic interference. The enclosure 12 may be formed from any suitable material such as plastic, metal or a composite material and may allow certain frequencies of electromagnetic radiation to pass through to wireless communication circuitry within the device 10 to facilitate wireless communication.

The enclosure 12 may further provide for access to various user input structures, depicted in FIG. 1 by reference numerals 14, 16, 18, 20, and 22. By way of these user input structures, a user may interface with the device 10, wherein each user input structure 14, 16, 18, 20, and 22 may be configured to control one or more device functions when pressed or actuated. By way of example, the input structure 14 may include a button that when pressed or actuated causes a home screen or menu to be displayed on the device.

The input structure 16 may include a button for toggling the device 10 between one or more modes of operation, such as a sleep mode, a wake mode, or a powered on/off mode, for example. The input structure 18 may include a dual-position sliding structure that may mute or silence a ringer in embodiments where the device 10 includes a cell phone application. Further, the input structures 20 and 22 may include buttons for increasing and decreasing the volume output of the device 10. It should be understood that the illustrated input structures 14, 16, 18, 20, and 22 are merely exemplary, and that the electronic device 10 may include any number of user input structures existing in various forms including buttons, switches, control pads, keys, knobs, scroll wheels, and so forth, depending on specific implementation requirements.

The electronic device 10 may further include a display 24 configured to display various images generated by the device 10. By way of example, the display 24 may be configured to display photos, movies, album art, and/or data, such as text documents, spreadsheets, text messages, and e-mail, among other things. The display 24 may also display various system indicators 26 that provide feedback to a user, such as power status, signal strength, call status, external device connections, or the like. The display 24 may be any type of display such as a liquid crystal display (LCD), a light emitting diode (LED) display, an organic light emitting diode (OLED) display, or other suitable display. In certain embodiments, the device 10 may include a touch sensitive element, such as a touch screen interface (not shown in FIG. 1) disposed adjacent to the display 24 that may function as an additional user input structure (e.g., in addition to structures 14, 16, 18, 20, and 22). By way of this touch screen interface, a user may select elements displayed on the display 24 such as, for example, by touching certain elements using the user's finger or a stylus.

As further shown in the present embodiment, the display 24 may be configured to display a graphical user interface ("GUI") 28 that allows a user to interact with the device 10. The GUI 28 may include various graphical layers, windows, screens, templates, elements, or other components that may be displayed on all or a portion of the display 24. For instance, the GUI 28 may display a plurality of graphical elements, depicted here generally as icons 30. By default, such as when the device 10 is first powered on, the GUI 28 may be configured to display the illustrated icons 30 as a "home screen," represented herein by the reference numeral 29. In certain embodiments, the user input structures 14, 16, 18, 20, and 22, may be used to navigate through the GUI 28 and, accordingly, away from the home screen 29. For example, one or more of the user input structures may include a wheel structure that may allow a user to select various icons 30 displayed by the GUI 28. Additionally, the icons 30 may also be selected via the touch screen interface.

The icons 30 may represent various layers, windows, screens, templates, elements, or other graphical components that may be displayed in some or all of the areas of the display 24 upon selection by the user. Furthermore, the selection of an icon 30 may lead to or initiate a hierarchical screen navigation process. For instance, the selection of an icon 30 may cause the display 24 to display another screen that includes one or more additional icons 30 or other GUI elements. Also, as shown in the present embodiment, each graphical element 30 may have one or more textual indicators 32 associated therewith, which may be displayed on or near its respective graphical element 30 to facilitate user interpretation of each graphical element 30. For example, the icon 34 may represent a Quick Response Code (hereinafter referred to as a "QR code") reader application and be associated with the textual indicator "QR Reader." It should be appreciated that the GUI 28 may include various components arranged in hierarchical and/or non-hierarchical structures.

When an icon 30 is selected, the device 10 may be configured to initiate, open, or run an application associated with the selected icon 30 and to display a corresponding screen. For example, when the icon 34 is selected, the device 10 may open the QR reader application. It should be understood that for each application provided on the device 10, one or more respective screen or screens may be displayed on the display 24 that may include various user interface elements corresponding to a respective application.

The electronic device 10 may also include various input/output (I/O) ports, such as the illustrated I/O ports 36, 38, and 40. These I/O ports may allow a user to connect the device 10 to or interface the device 10 with one or more external devices. For example, the input/output port 36 may include a proprietary connection port for transmitting and receiving data files, such as media files. The input/output port 38 may include a connection slot for receiving a subscriber identify module (SIM) card, for instance, where the device 10 includes cell phone functionality. The input/output port 40 may be an audio jack that provides for connection of audio headphones or speakers. As will appreciated, the device 10 may include any number of input/output ports configured to connect to a variety of external devices, such as to a power source, a printer, and a computer, or an external storage device, just to name a few. As will appreciated, the I/O ports may include any suitable interface type such as a universal serial bus (USB) port, serial connection port, FireWire port (IEEE-1394), or AC/DC power connection port.

Certain I/O ports may be configured to provide for more than one function. For instance, in one embodiment, the I/O port 36 may be configured to not only transmit and receive data files, as described above, but may be further configured to couple the device to a power charging interface, such as an power adaptor designed to provide power from a electrical wall outlet, or an interface cable configured to draw power from another electrical device, such as a desktop computer. Thus, the I/O port 36 may be configured to function dually as both a data transfer port and an AC/DC power connection port depending, for example, on the external component being coupled to the device 10 through the I/O port 36.

The electronic device 10 may also include various audio input and output elements. For example, the audio input/output elements, depicted generally by reference numeral 42, may include an input receiver, which may be provided as one or more microphones. For instance, where the electronic device 10 includes cell phone functionality, the input receivers may be configured to receive user audio input such as a user's voice. Additionally, the audio input/output elements 42 may include one or more output transmitters. Thus, where the device 10 includes a media player application, the output transmitters of the audio input/output elements 42 may include one or more speakers for transmitting audio signals to a user, such as playing back music files, for example. Further, where the electronic device 10 includes a cell phone application, an additional audio output transmitter 44 may be provided, as shown in FIG. 1. Like the output transmitter of the audio input/output elements 42, the output transmitter 44 may also include one or more speakers configured to transmit audio signals to a user, such as voice data received during a telephone call. Thus, the input receivers and the output transmitters of the audio input/output elements 42 and the output transmitter 44 may operate in conjunction to function as the audio receiving and transmitting elements of a telephone.

In some embodiments of the technology, an electronic device may include one or more front-, side-, and/or rear-facing cameras. In the illustrated embodiment, the electronic device 10 further includes a front-facing camera 46.

Figure 2:
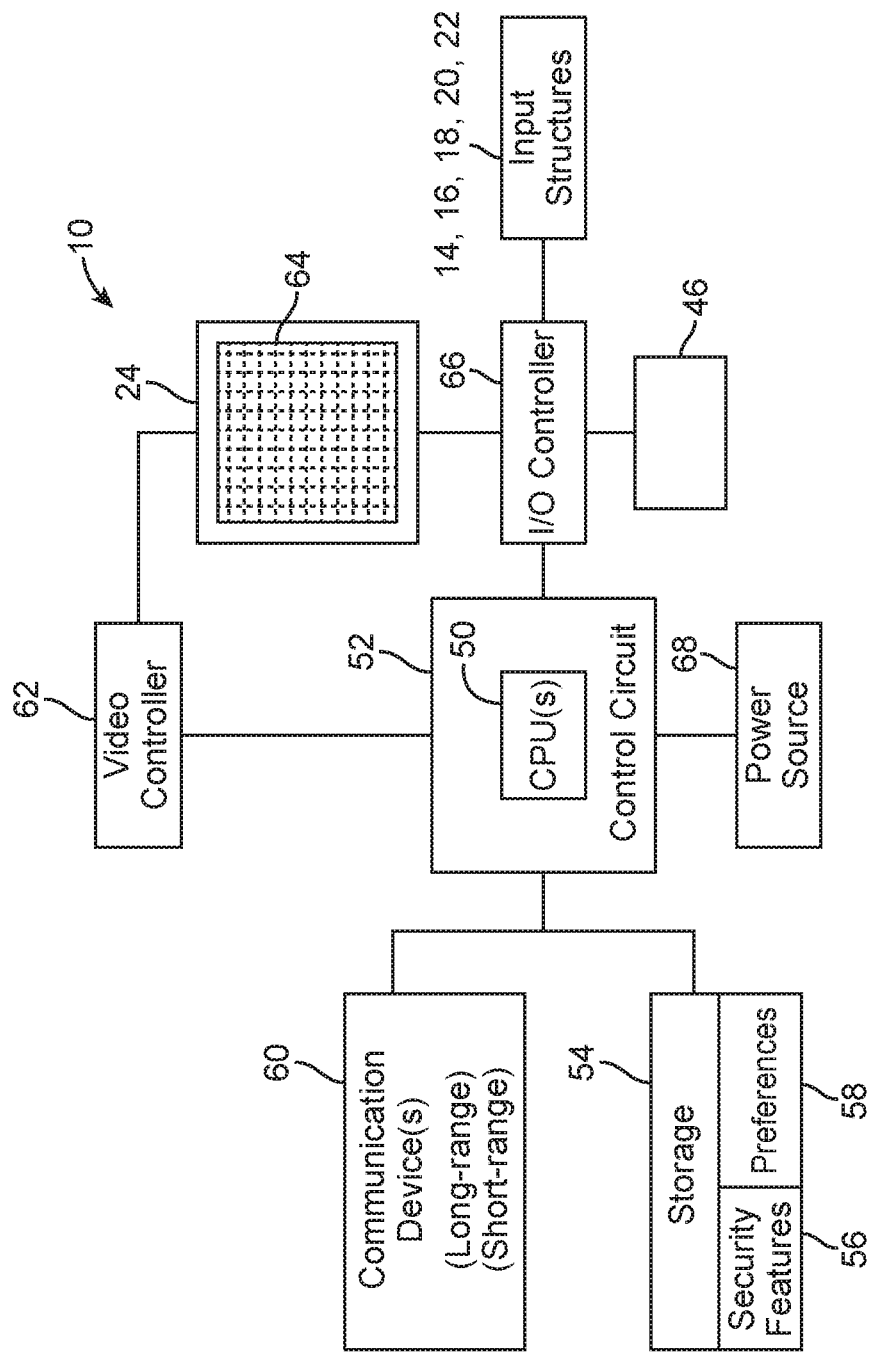
FIG. 2 is a simplified block diagram of the device of FIG. 1 in accordance with some embodiments of the present technology.

Additional details of the illustrative device 10 may be better understood through reference to FIG. 2, which is a block diagram illustrating various components and features of the device 10 in accordance with one embodiment of the present technology. As shown in FIG. 2, the device 10 may include the above discussed display 24, as well as a CPU 50, control circuitry 52, a storage device 54, one or more communication interfaces 60, a video controller 62, a touch screen interface 64, an I/O controller 66, and a power source 68.

The operation of the device 10 may be generally controlled by the central processing unit (CPU) 50 and the control circuit 52. In cooperation, these elements may provide the processing capability required to execute an operating system, application programs, the GUI 28, and any other functions provided on the device 10. The CPU 50 may include a single processor or, in other embodiments, it may include a plurality of processors. By way of example, the CPU 50 may include "general purpose" microprocessors, a combination of general and application-specific microprocessors, instruction set processors, graphics processors, video processors, as well as related chips sets and/or special purpose microprocessors. The control circuit 52 may include one or more data buses for transferring data and instructions between components of the device 10. The control circuit 52 also may further include on board memory (RAM) for caching purposes. Additionally, although not illustrated in FIG. 2, the device 10 may include a standalone random access memory (RAM) in communication with the CPU 50 by way of one or more memory controllers, which may be integrated within the control circuit 52.

Information used by the CPU 50 may be stored within a long-term storage device, represented by reference numeral 54. The storage device 54 of the electronic device 10 may be utilized for storing data required for the operation of the CPU 50, data to be processed or executed by the CPU 50, as well as other data required by the device 10, such as application and program data. For, example, the storage device 54 may be configured to store the firmware for the electronic device 10 that is used by the CPU 50. The firmware may include an operating system, as well as other programs or drivers that enable various functions of the electronic device 10, GUI functions, and/or processor functions. The storage device 54 may also store components for the GUI 28, such as graphical elements, screens, and templates. Additionally, the storage device 54 may store data files such as media (e.g., music and video files), image data, application software, preference information (e.g., media playback preferences, general user preferences), financial account information, network connection information (e.g., information that may enable the device 10 to establish a wireless connection, such as a telephone or Internet connection), subscription information (e.g., information that maintains a record of podcasts, television shows or other media to which a user subscribes), telephone information (e.g., telephone numbers), and any other suitable data required by the device 10. The long term storage 54 may be non-volatile memory such as read only memory, flash or solid state memory, a hard disk drive, or any other suitable optical, magnetic, or solid-state computer readable media, as well as a combination thereof.

The device 10 may include one or more network communication devices 60 for providing additional connectivity channels for receiving and transmitting information. For example, the communication device 60 may represent one or more network interface cards (NIC) and/or a network controller as well as various associated communication protocols. The communication device 60 may provide for various long-range communication interfaces, such as a wireless local area network (WLAN) interface (e.g., an IEEE 802.11x wireless network), a local area network (LAN) interface, or a wide area network (WAN) interface. By way of example, a WAN interface may permit a private and/or secure connection to a cellular data network, such as the Enhanced Data rates for GSM Evolution (EDGE) network or the 3G network (e.g., based on the IMT-2000 standard). The network communication device 60 may further provide a short message service (SMS) interface.

In certain embodiments, the electronic device 10 may include a service discovery networking protocol to establish a connection with an external device through a network interface. For example, both the device 10 and the external device may broadcast identification information using internet protocol standards (IP). In some embodiments, the external device may additionally broadcast information relating to the available services the external device is capable of providing (e.g., printing services for a networked printer). The devices may then use the identification information to establish a network connection, such as a PAN connection or a WLAN connection, between the devices. By way of example, a device identification protocol may be provided by Bonjour®, developed by Apple Inc.

User preference settings 58, which may be stored in the storage device 54, may further determine properties of the above-mentioned communication interfaces provided by the network communication device 60. For instance, the preferences 58 may include a list of networks that the device 10 may connect to and may further govern the order or priority between the communication interfaces. Further, the communication preferences associated with the preferences 58 may be further dependent upon security features 56 available for each respective communication interface. The security features 56 may be stored in the storage device 54 and may include one or more cryptographic protocols, such as a secure sockets layer (SSL) protocol or a transport layer security (TLS) protocol, for establishing secure communications between the device 10 and an external device.

The security features 56 may also include a secure access-restricted storage area (e.g., within the storage device 54) to limit access to the sensitive data, such as encryption keys, passcodes and passwords, digital certificates, or the like. Additionally, in some embodiments, the secure storage area 56, in addition to storing the above-mentioned sensitive data, may be further protected by its own respective password or authorization "personal identification number" (PIN), for example, in order to prevent unauthorized access to the information stored therein.

The device 10 may also include the video controller 62, which may be operatively coupled to the display 24 and configured to receive image data and to send voltage signals corresponding to the pixel values of the image data to the display 24. The displayed image data may be representative of information received through the communication interface, as well as information contained in the storage device 54. As will be understood by those skilled in the art, pixel values may be numerical assignments corresponding to respective pixel intensities. Thus, the display 24 may receive the voltage signals from the video controller 62 as an input and produce an image corresponding to the voltage signals. For instance, an image produced by the signals provided by the video controller 62 may represent a screen of the GUI 28 described above with reference to FIG. 1.

As discussed above, a user operating the device 10 may select various graphical elements which may represent applications or information that may be displayed through the GUI 28. A touch screen interface 64 may be positioned in front of or behind the display 24 and may provide a user the ability to select graphical elements, such as the icons 30 displayed by the GUI 28 described above in FIG. 1. The touch screen interface 64 may be configured to receive inputs based on a physical contact (e.g., touching the display 24) either by the user or an object (e.g., stylus) being controlled or manipulated by the user, and to send "touch event" information to the CPU 50. The CPU 50 may then process the detected touch event information and perform a corresponding action. For instance, referring briefly back to FIG. 1, the "touching" of the icon 34 may be processed by the CPU 50 as an instruction to execute or initiate the corresponding electronic wallet application. The touch screen interface 64 may employ any suitable type of touch screen technology such as resistive, capacitive, infrared, surface acoustic wave, electromagnetic, or near field imaging. The touch screen interface 64 may also employ single point or multipoint sensing.

The I/O controller 66 depicted in FIG. 2 may provide an infrastructure for allowing a user to communicate with the CPU 50 through various input structures provided on the device 10, such as the input structures represented by the reference numerals 14, 16, 18, 20, and 22 in FIG. 1. The user input structures 14, 16, 18, 20, and 22 may be used in conjunction with, or independently of, the touch screen interface 64 to provide input information to the device 10. The I/O controller 66 is also coupled with a camera 46.

The power source 68 of the device 10 may include the capability to power the device 10 in both non-portable and portable settings. For example, in a portable setting, in order to facilitate transport and ease of motion, the device 10 may include an integrated power source 68 for powering the device 10. The power source 68 may include one or more batteries, such as a Li-Ion battery, which may be user-removable or secured to the enclosure 12. In certain embodiments, the proprietary connection I/O port 36 may be used to connect the device 10 to a power source for recharging the battery. In other embodiments, the one or more batteries may be non-integrated and may include one or more rechargeable or replaceable batteries. Further, in a non-portable setting, the power source 68 may include AC power, such as provided by an electrical outlet.

As discussed above, the device 10 includes a camera 46. Accordingly, the present technology solves the problems identified above by making it possible to transfer sensitive information, transfer money, pay for goods and services, etc. using mobile devices equipped with a camera.

Figure 3:
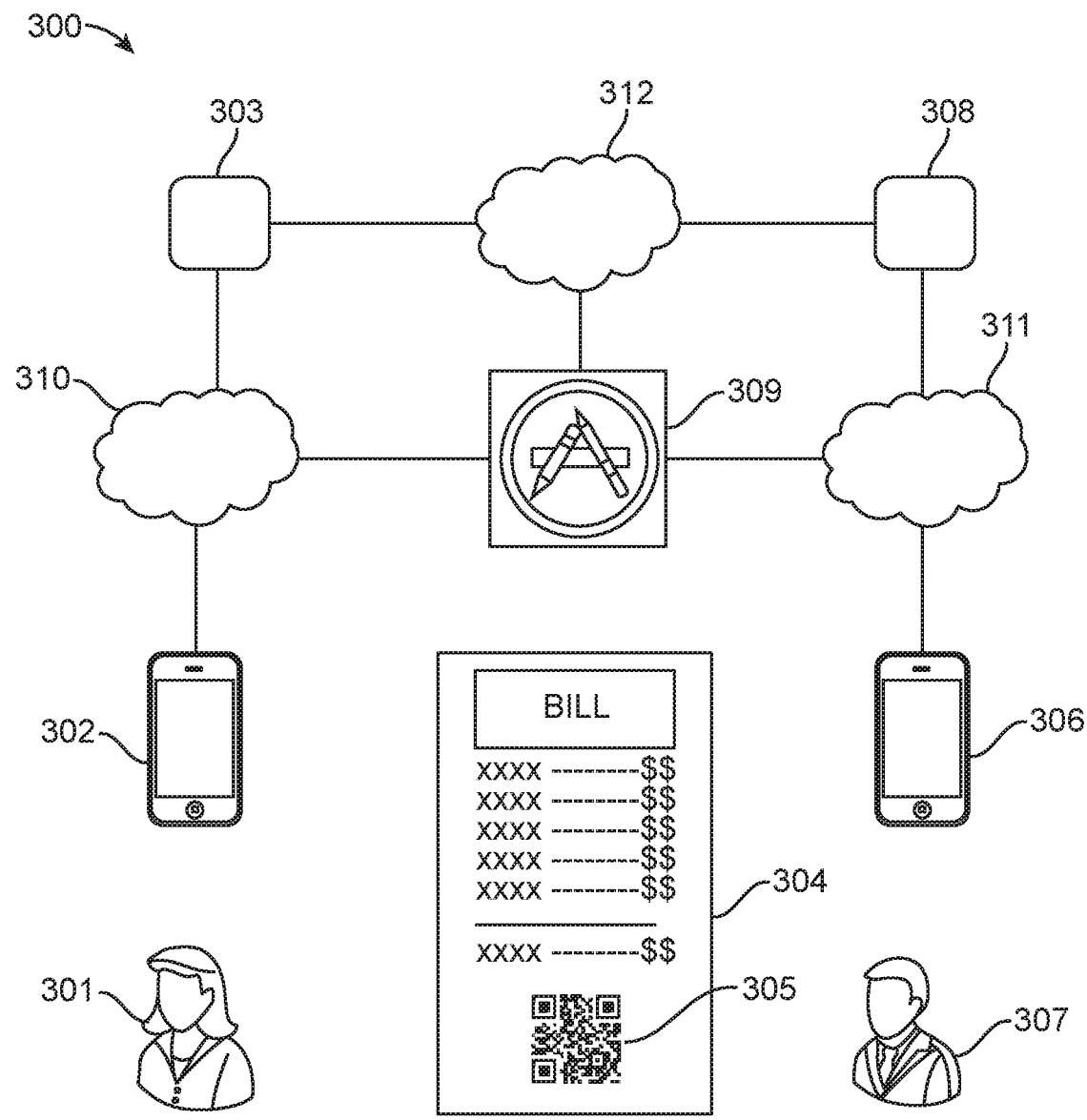
FIG. 3 illustrates a system configured for enabling merchants and customers to conduct secure, cashless financial transactions according to some embodiments of the present technology.

FIG. 3 illustrates a system 300 configured for enabling merchants and customers to conduct cash-less financial transactions using a paper bill, a mobile device equipped with a camera, an optical code, and one or more cloud-based clearinghouse according to some embodiments of the present technology. While specific mobile devices are described throughout this description, it will be apparent to those having ordinary skill in the art and the benefit of the disclosure that any device with the capability of capturing optical data and interfacing with a network can be used to achieve the same beneficial results.

As shown, the system 300 of FIG. 3 includes a merchant 301 operating a mobile device 302 and performing a transaction with a customer 307 also running a mobile device 306. Before initiating a camera-based optical transaction, the merchant 301 must first create a verified account with a transaction clearinghouse 303 or similar institution and configure an application on her mobile device 302 to perform an optical-based transaction. In some embodiments of the technology, a necessary application resides on network-based application distribution platform 309, such as iTunes® or the AppStore.sup.SM, available from Apple Inc. of Cupertino, Calif. Similarly, for a customer 307 to benefit from the merchant's ability to conduct optical payments, the customer also must have a verified account with an optical-based transaction clearinghouse 308 or similar institution and an appropriate application installed on his mobile device 306.

As shown, the clearinghouse 303 and the clearinghouse 308 comprise separate institutions; however, those having ordinary skill in the art will appreciate that the clearinghouses can be the same institution or a subsidiary, partner, division, etc. of the same institution. Also shown are networks 310, 311, and 312 coupling merchants 301 and customers 307 to the clearinghouses 303, 308 and to the network based application distribution platform 309. Those having ordinary skill in the art will also readily understand the networks 310, 311, and 312 can be the same network or different networks.

Once the merchant 301 has configured her device 302 with the necessary application and has created a verified account, she can begin recording transactions, (i.e. bills, invoices, prescriptions, etc.) on her mobile device 302. In some embodiments of the present technology, invoice creation comprises an individual simply listing an invoice amount and a note regarding what goods are being sold or leased or what services are being performed. In some embodiments, a more detailed invoice is created that includes auxiliary data such as type and quantity of items purchased. Although specific examples of invoices are described herein, it will be readily apparent to those with ordinary skill in the art having benefit of this disclosure that any type of agreement or contract can be memorialized using the present technology.

In some embodiments of the present technology, the application for performing an optical-based transaction obtained from the network-based application platform 309 comprises a graphical user interface for facilitating the process of invoice creation.

Once an invoice is created, the merchant 301 can upload the transaction data to the clearinghouse 303 along with a claim number that is recognizable by the clearinghouse 303. The merchant 301 then presents a transaction receipt 304 (i.e. a bill) to the customer 307—either in printed form or on a display device. The receipt 304 includes an optical code 305 that encodes the claim number and an identification of the clearinghouse 303 at which the transaction has been stored.

The customer 307 can then capture the optical code 305 on the receipt 304 and pull the data from clearinghouse 308 or clearinghouse 309. If the merchant 301 and the customer 307 have different clearinghouses, the clearinghouse 308 and the clearinghouse 309 communicate with one another directly or via a network 312. The customer 307 can then satisfy the receipt 304 through the clearinghouse 308.

Some embodiments of the present technology involve the customer 307 satisfying the transaction via a one-time payment to the clearinghouse 308. According to these embodiments, the merchant 301 is told when the customer 307 satisfies the receipt 304, but the customer's payment information is kept anonymous from the merchant 301. Some embodiments of the present technology involve the customer 307 creating an account with the clearinghouse 308 for performing one or more banking and/or e-commerce services.

Figure 4:
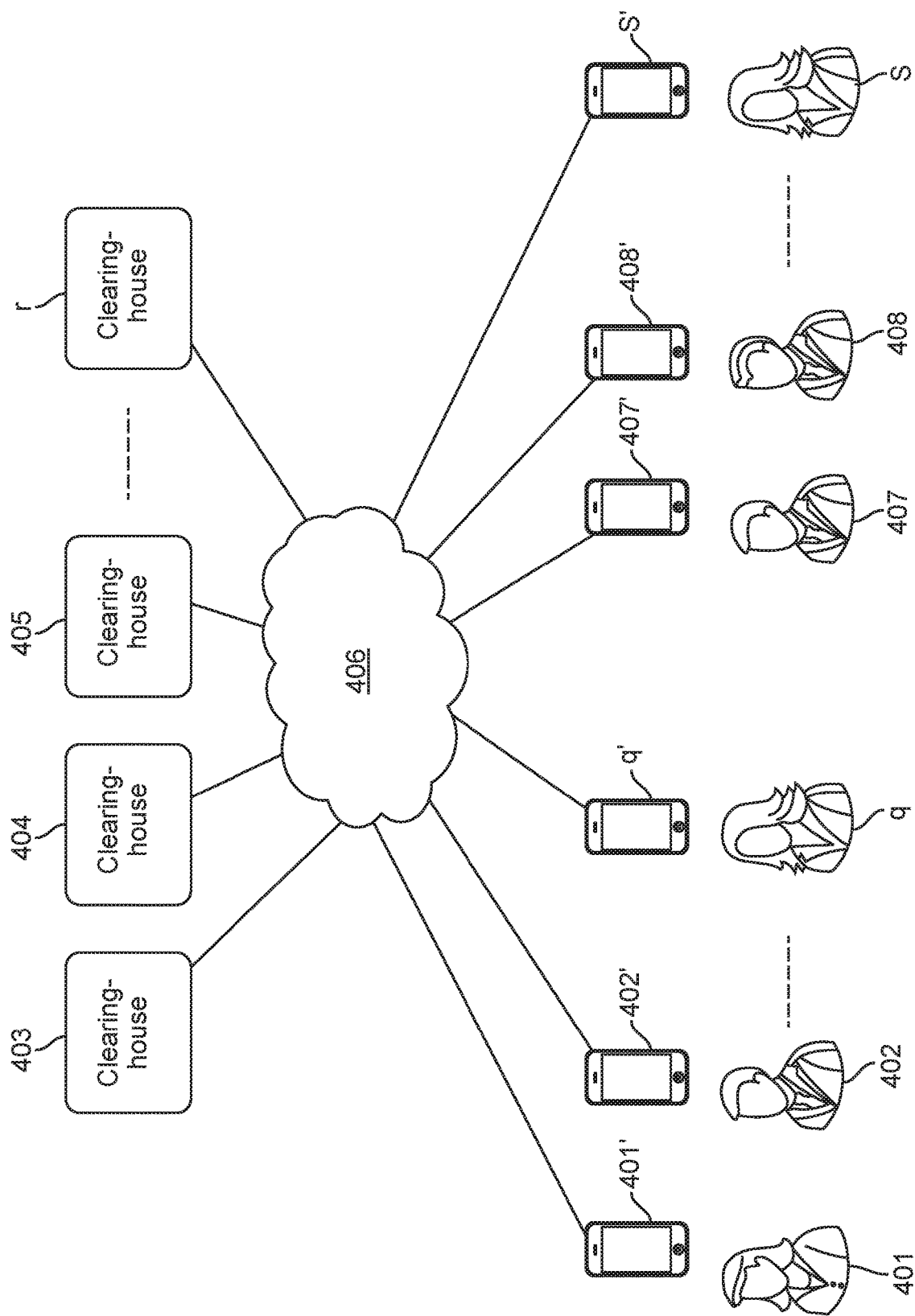
FIG. 4 illustrates a system configured for enabling a plurality of merchants and a plurality of customers to conduct secure, cashless financial transactions according to some embodiments of the present technology.

Some embodiments of the present technology involve many merchants and service providers and many customers performing transactions using optical coupling and one or more clearinghouses. FIG. 4 illustrates a system 400 configured for enabling a plurality of merchants and a plurality of customers to conduct financial transactions using devices equipped with a camera, an optical code, and one or more cloud-based clearinghouses according to some embodiments of the present technology. According to FIG. 4, a plurality of merchants or service providers 401, 402, . . . , q communicate with one or more clearinghouses 403, 404, 405, . . . , r via a network 406 and a mobile device 401', 402', . . . , q'. Likewise, a plurality of customers 407, 408, . . . , s communicate with the one or more clearinghouse 403, 404, 405, . . . , r via the network 406 and a mobile device 407', 408', . . . , s'. According to the arrangement of FIG. 4, an invoicing and confidential payment transaction system using optical coupling can be extended and scaled to a large group of users.

Figure 5:
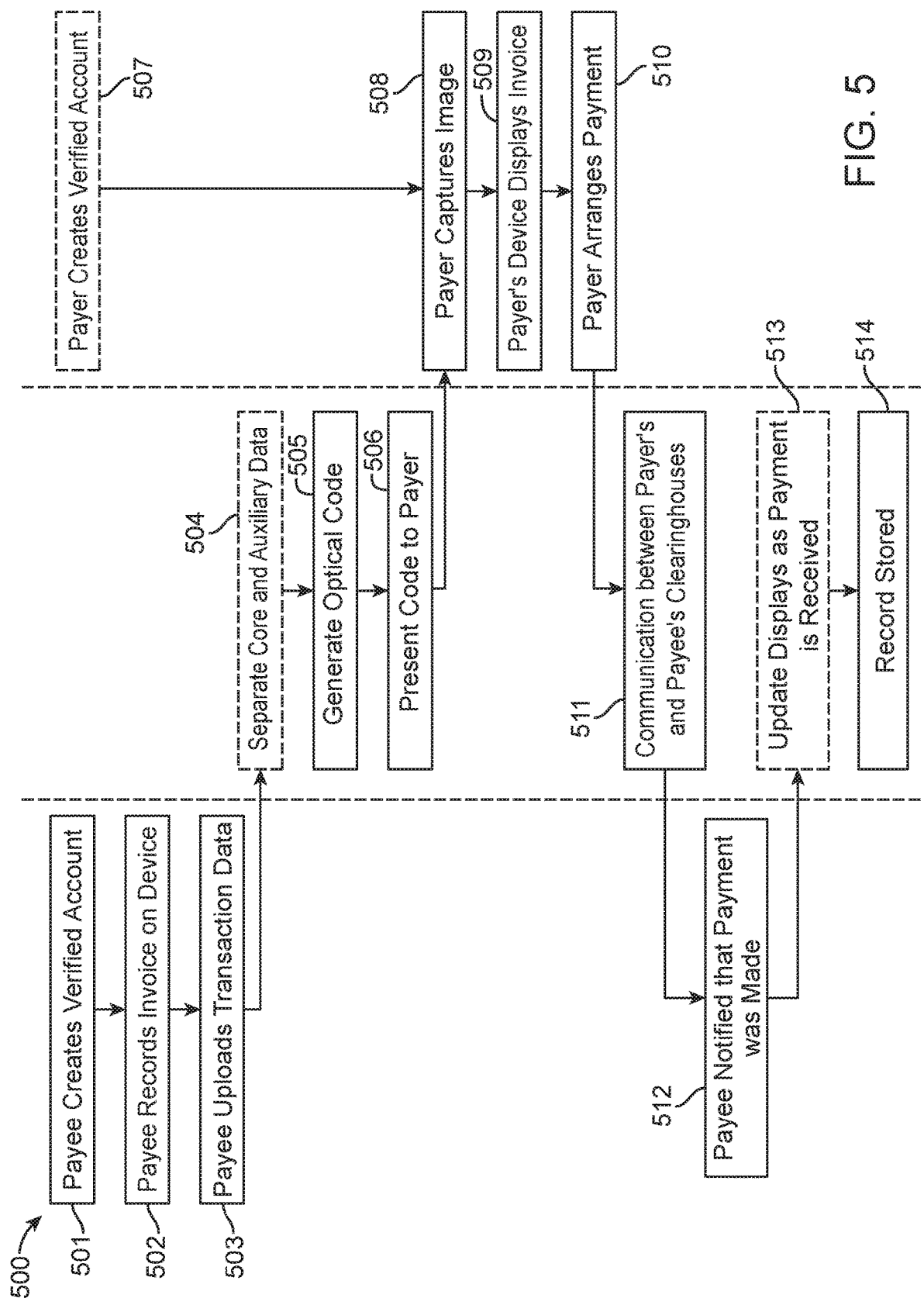
FIG. 5 illustrates a method of performing an invoicing and confidential payment transaction between parties using optical coupling according to some embodiments of the present technology.

A method of performing a transaction using optical coupling is described in more detail in connection with FIG. 5. FIG. 5 illustrates a method 500 of performing an invoicing and confidential payment transaction between parties using optical coupling according to some embodiments of the present technology. The method 500 begins with a payee creating an account with an on-line financial transaction clearinghouse 501. In some embodiments of the present technology, creating an account involves registering the payee's identification information (i.e. business name, address, contact information, etc.), information regarding how to tender payment (i.e. bank account numbers, PayPal routing information, etc.), and account settings and preferences. Account creation can also involve the exchange of public and private encryption keys or similar cryptography methods. Similarly, the process of a payee creating an account can also involve one or more security measures to ensure that the payee is the owner of a financial account. For example, a clearinghouse might require that the payee confirm a nominal amount of money being withdrawn and subsequently deposited into his account before the account is verified.

After the payee creates an account, the method 500 continues with the payee memorializing an invoice 502 on a device. The case of merchants, this can include auxiliary data, such as type and quantity of items purchased. In the case of person to person to transactions, this may be as simple as a financial amount and a note concerning the transaction. For example, in a restaurant setting, a waitress can take a table's order and input the items into a wired terminal to memorialize the invoice. In another example, a service provider can memorialize an invoice as he provides services by inputting time entries into a mobile device. Those with ordinary skill in the art having the benefit of the disclosure will readily appreciate that a wide variety of input types and devices, now known or later developed, can be used to memorialize invoices.

Next, the payee finalizes the invoice and transfers the transaction data to a clearinghouse 503 along with a unique claim number that identifies the transaction. In some embodiments, the uniqueness of the claim number is ensured by electronically requesting a unique number from the clearinghouse. In some embodiments, the claim number is generated by a previously-agreed upon protocol between the clearinghouse and the payee. In some embodiments of the technology, the clearinghouse inspects a payee's encryption key to determine the authenticity of the transaction.

Optionally, the clearinghouse separates 504 the payee-submitted invoice into core data (such as the amount to be paid) and auxiliary data (such as the type and quantity of items) and posts them to separate servers. By doing so, the clearinghouse avoids having or re-submitting visibility into the actual goods that are being bought or sold. For example, suppose a couple shares a clearinghouse account and one partner wants to surprise the other with a gift. The merchant selling the gift can invoice the clearinghouse with the price and description, but the clearinghouse can strip the auxiliary description from the invoice so that when code is sent to the couple's shared account, it will merely reflect an amount to be paid without ruining the surprise. Such optional splitting can be used to enhance customer privacy. The clearing house (or optionally when there are multiple clearing houses, all clearing houses except trusted ones such as the one that the customer has an account with) do not have access to the auxiliary data and are unable to data-mine the customer's transactions or develop profiles of the actual products the customer purchases. Consequently, the server hosting the auxiliary data does not know the individual with whom the data is associated. So it may be able to suggest promotional material directly related to the transaction, but is unable to track and profile the customer since the server is unable to form connections between a multitude of unique claim numbers and the individual customers that are responsible for each transaction.

Once the clearinghouse has invoice information and a unique identifier, it generates an optical code 505 that, upon recognition, links a client device to the transaction details. Some embodiments of the present technology involve generating a Quick Response Code (hereinafter referred to as a "QR code") that is readable by a QR code reader application. However, those with ordinary skill in the art having the benefit of this disclosure will understand that any easily identifiable imaging scheme may be used instead of a QR code. For example, a code can simply be manually keyed in by a user. Additionally, a barcode could be used. Alternatively, an easily identifiable border may be displayed and the claim number may be simply presented in a standard font as human and computer readable characters and recovered from the image using optical character recognition. Alternately, a small but easily processed image may be presented as the claim token within a border that makes it easy to scan for imaging software. The key idea is that the claim number associated with the transaction is presented optically and recognized using a camera and imaging software.

The method 500 continues with the payee presenting the payer with a representation of the optical code 506 that encodes the unique claim number and designates the clearinghouse at which the claim has been filed. In some embodiments, the representation of the optical code comprises a paper receipt with the optical code. In some embodiments, the optical code is transmitted to a payer via an electronic medium and comprises an electronic representation of the optical code. In some embodiments, the electronic representation of the optical code is transmitted to the payer by presenting the payer with an electronic device that displays the optical code. In some embodiments, the electronic representation of the optical code is transmitted from a payee device to a payer device via email, SMS, MMS, etc. In some embodiments, the optical code is transmitted to a payer's device via electromagnetic coupling, such as a wireless network connection, Bluetooth connection, or near field communications coupling. The optical code may be accompanied with any or all auxiliary data.

Optionally, the payer creates an account 507 in advance of receiving a QR-embedded invoice. The method 500 continues with the payer capturing an image 508 of the optical code and converts it back to the transaction details. The payer uses secure communication with the clearinghouse to pull the core data and auxiliary data associated with the transaction. If the payer and payee have different clearinghouses, the different clearinghouses communicate with each other to supply the payer with the relevant data. The payer's clearinghouse then verifies the identity of who originated that unique claim number, i.e., they look up the owner of the account that the payment will be credited to ensure that the payment will go to the payee or someone authorized to take payments on the payee's behalf.

Next, the payer's device displays 509 the invoice data, the auxiliary data (i.e. the amount, type of goods, etc.) if any, and who the payment will go to. Accordingly, the user can visually verify the invoice to check that the quoted price is the price being charged. Additionally, the user can verify the identity of the party that they are making payment to, thereby avoiding paying a party impersonating the true seller. When the user is satisfied, he authorizes payment 510 using his device.

Some embodiments of the present technology involve an interface for allowing the payer to authorize partial payment. For example, the case of a restaurant bill for a group, each guest may individually scan the receipt using their own device and then just authorize the payment for the items they ordered, along with their share of taxes, gratuity etc.

Next, the payer's device signals authorization back to the clearinghouse. In the case of more than one clearinghouse, the method 500 facilitates communication and reconciliation between the multiple clearinghouses 511 and the one or more clearinghouses signal back to the payee that full or partial payment has been received in the payee's account 512. Optionally, all devices involved in the transaction update their displays of the payment as it progresses 513. Finally, the clearinghouse or clearinghouses record the fully-satisfied transaction 514. In some embodiments, wither the payer's or the payee's device optionally saves the receipts for later use and records/returns etc. In some embodiments, only the core data is saved.

According to the present technology, it is not necessary for the payee to know the identity of the payer; rather, it is only necessary for the payee to be assured by the clearinghouse that the bill has been paid. In this way the technology preserves the anonymous nature of cash payment as far as the payer's privacy is concerned and at the same time records the payee's side of the transaction for record keeping such as for taxes. Additionally, no sensitive information is exchanged between the parties. There are no credit card numbers or personal information that can be stolen. The payee cannot store the payer's financial information. Indeed, once the transaction has been completed, the printed receipt may be discarded without the risk of theft or leaked personal information.

As explained above, the present technology preserves the anonymous nature of a cash payment and offers the convenience of mobile payment. An especially illustrative example of the utility and convenience of the present technology can be seen in the case of a group of people splitting a bill at a restaurant.

Figure 6:
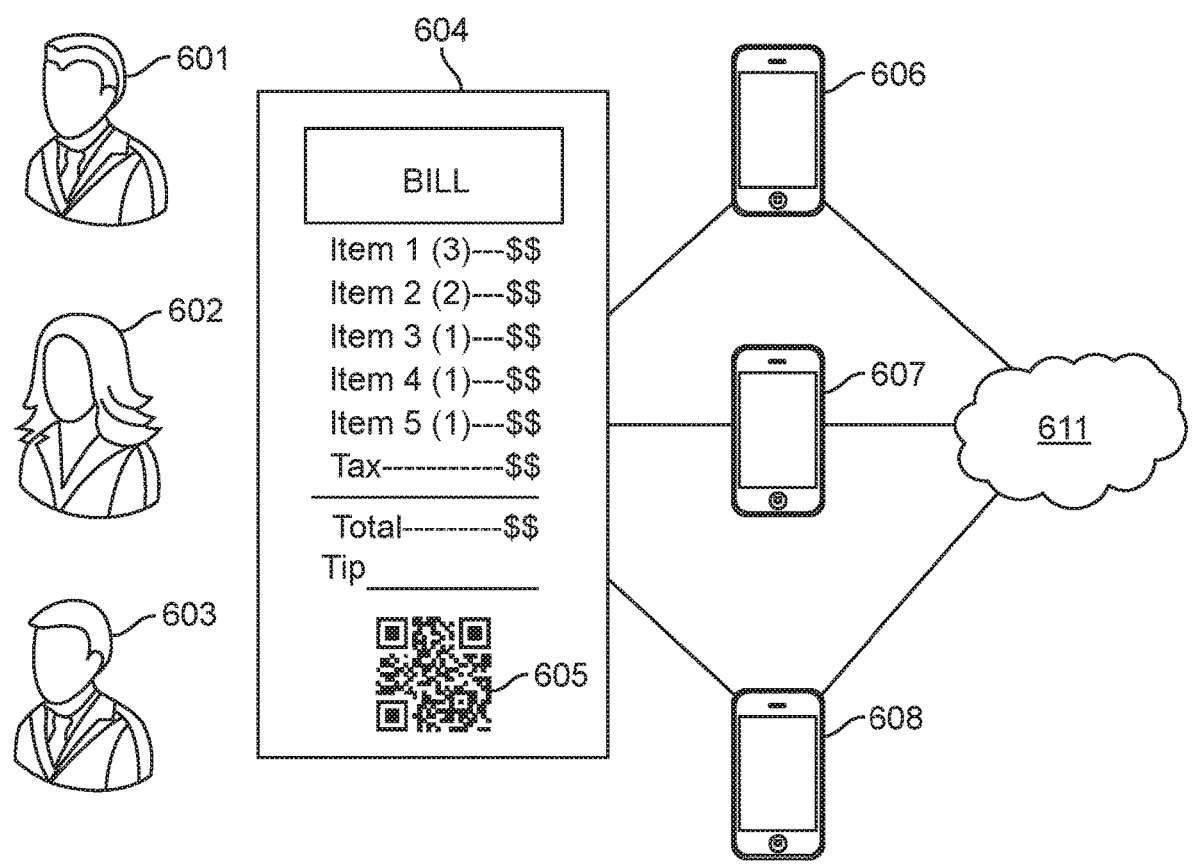
FIG. 6 illustrates a graphical representation of a group of diners splitting a bill using a payment system of optical coupling according to some embodiments of the present technology.
Figure 6:
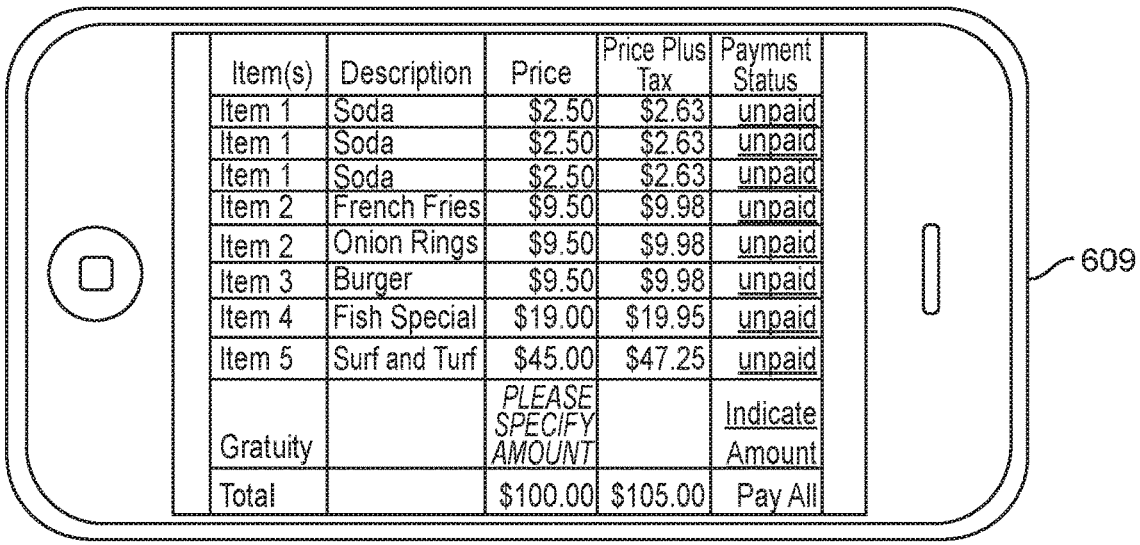
Figure 6:
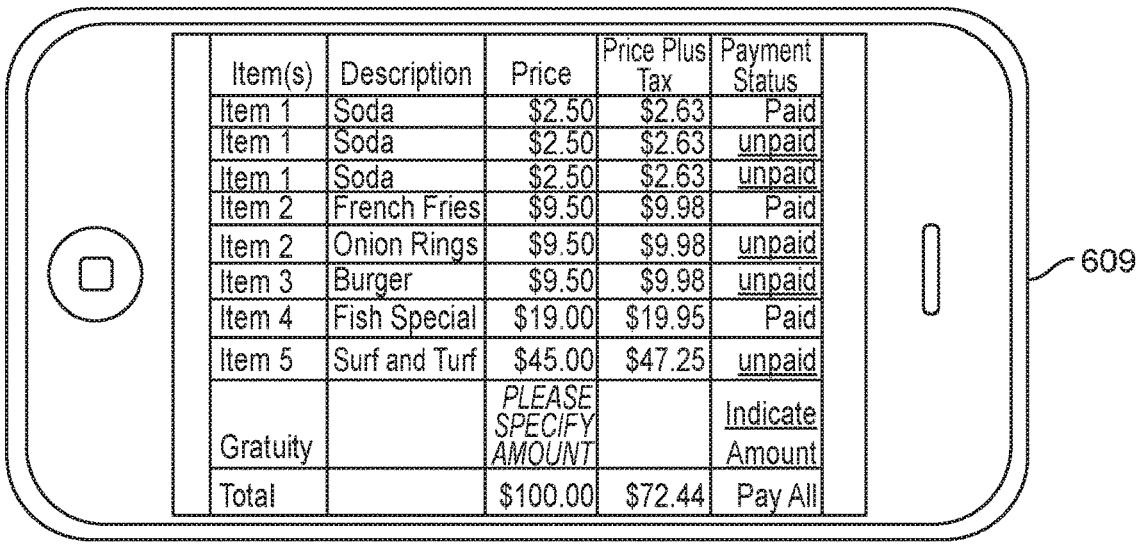
Figure 6:

FIG. 6 illustrates a graphical representation of a group of diners 601, 602, 603 splitting a bill 604 using a payment system of optical coupling according to some embodiments of the present technology. According to FIG. 6, a paper bill 604 is presented to the group of diners 601, 602, 603. The paper bill 604 itemizes the diners' order, describes the items served, lists the price of the individual items, lists the sales tax associated with the bill, lists the total price, and provides the diners the opportunity to tip their server. Additionally, the paper bill 604 includes an optical code 605 printed thereon. According to the present technology, the diners can scan the optical code with a camera in their respective mobile devices 606, 607, 608 to access the billing information via a clearinghouse server (not shown) available via one or more networks 611 that the merchant has an account with.

According to the present technology, a diner's 601 mobile device 606 recognizes the optical code 605 and displays an electronic representation 609 of the bill 604 via an interface on the diner's 601 mobile device 606. In some embodiments of the present technology, the electronic representation of the bill 604 is displayed to users via a browser-based interface. In some embodiments, the user pre-installs a dedicated optical code reader application configured for presenting electronic bills in an elegant and user-friendly interface. In some embodiments, the dedicated application is available for download from a network-based application platform, such as the AppStore.sup.SM, available from Apple Inc. of Cupertino, Calif.

Like the paper bill 604, the electronic representation of the paper bill 604 itemizes the diners' order, describes the items served, lists the price of the individual items, lists the sales tax associated with the items, lists the total price, and provides the diners the opportunity to tip their server. Additionally, according to some embodiments of the present technology, the electronic representation 609 of the paper bill 604 includes executable links that allow users to select items that they would like to pay for, indicate their share of the total gratuity that they would like to pay, or indicate that they want to pay for the entire bill.

In some embodiments of the present technology, the electronic representation 609 of the paper bill 604 dynamically adjusts as individual diners pay for items. For example, suppose that first diner 601 accepts the paper bill 604 and is the first to scan the optical code 605. Using the executable links, the first diner 601 pays for his share of the bill and passes the paper bill 604 to another diner 602. When the second diner 602 scans the optical code 605, the electronic representation 609 will have dynamically adjusted to reflect the total amounts due minus the amounts from the items that the first user 601 paid for. Likewise, the second diner 602 pays her share and when the electronic representation 609 is displayed on the third diner's device 608, the remaining portion of the unsettled bill is displayed.

In some embodiments of the present technology, the payee is notified when any payment on the bill 604 is made—either partial or full payment. In some embodiments, the payee is simply informed that the bill has been completely settled.

Figure 7:
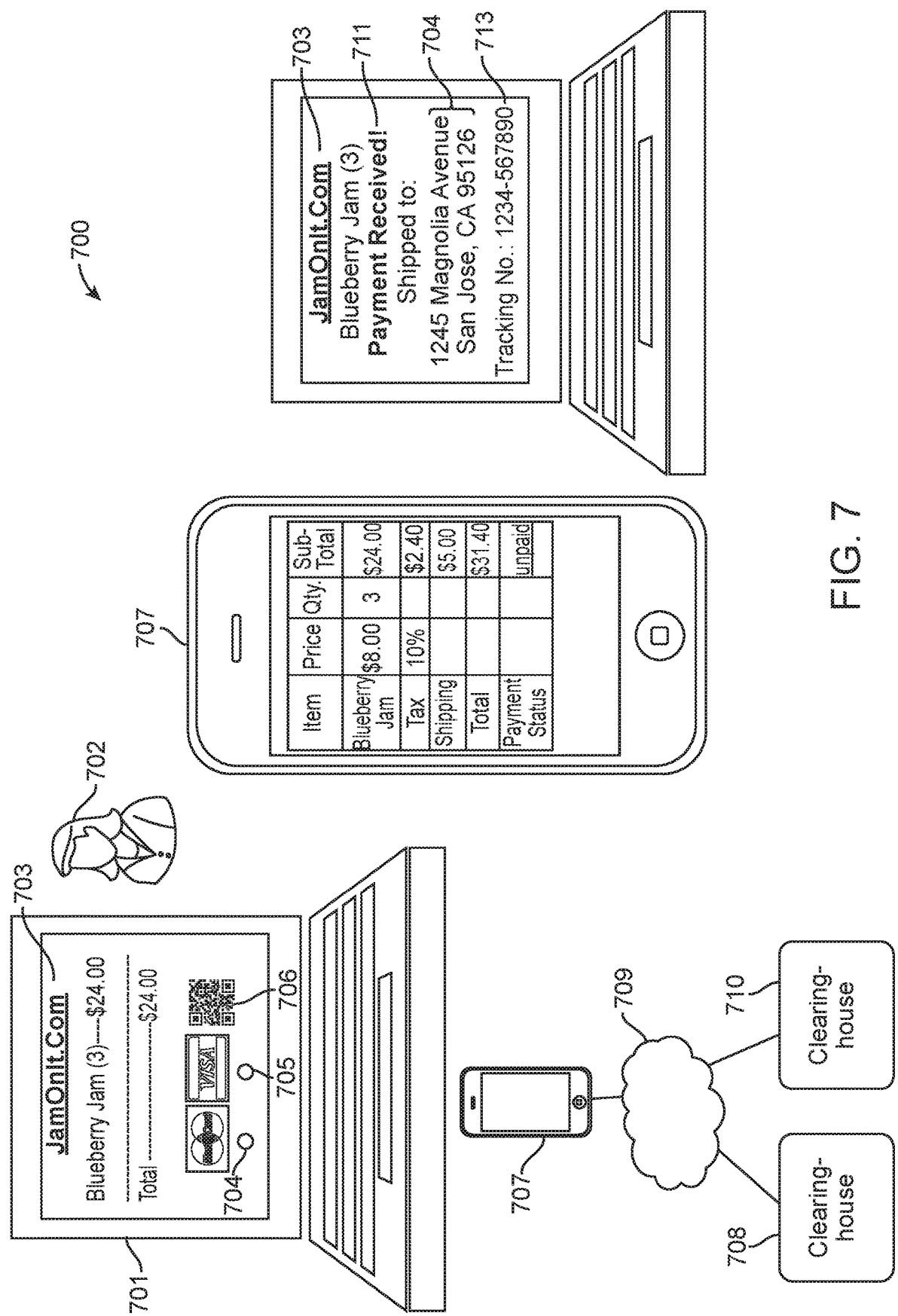
FIG. 7 illustrates a system for performing secure, optical-based financial transactions online according to some embodiments of the present technology.

The exemplary scenario describes how the present technology benefits users in a commercial setting, i.e. a restaurant. However, the present technology also benefits consumers performing financial transactions on-line in a browser-based interface. FIG. 7 illustrates a system 700 for performing secure, optical-based financial transactions online according to some embodiments of the present technology. As shown, the system 700 includes a user computer 701 connected to the internet. Also shown, a user 702 finds items online that she would like to purchase. Upon checking out of an online store 703, the user is typically presented with credit card payment options 704, 705. However, it is oftentimes the case that a user is skeptical of providing credit card information to an online store 703, especially if the online store 703 does not have a well-known, positive reputation. Consequently, the present technology provides the user 702 with a more secure payment option in the form of an optical code 706. According to these embodiments, the online store 703 never gains access to the user's 702 payment information, but merely receives verification that the user has indeed paid using the optical code 706.

According to the system 700 of FIG. 7, the online store 703 has a verified account with a clearinghouse 708 such that when a user 702 scans the optical code 706 using a camera on a network-connected device 707, the clearinghouse 708 sends the user payment information via one or more network 709 to the network-connected device 707. In some embodiments, the user already has a verified account with a clearinghouse 710 in which the clearinghouse 710 stores the user's payment information. Clearinghouses 707 and 710 can be the same or different entities. Next, the user 702 reconciles the payment using the network-connected device 707 by authorizing the clearinghouse 710 to make the payment without ever providing the online store 703 with sensitive financial information.

Also, in some embodiments of the present technology, the clearinghouse 710 contains a user profile for its users. For example, the clearinghouse 710 can store a user's 702 shipping address. Accordingly, when the user 702 authorizes payment to the online store 703, the online store is automatically supplied with the user's shipping information. Once a payment is successfully completed using the network-connected device 707, the online store 703 receives confirmation 711 that an item has been paid for and the user receives confirmation 712 that the items have been shipped and receives a tracking number 713.

As explained herein, the present technology benefits users by protecting sensitive financial information in various point-of-sale transactions. However, due to the fact that these transactions oftentimes require a network-connected device, the present technology also allows for various new mechanisms for serving promotional content to users that is highly relevant and interactive.

Figure 8:
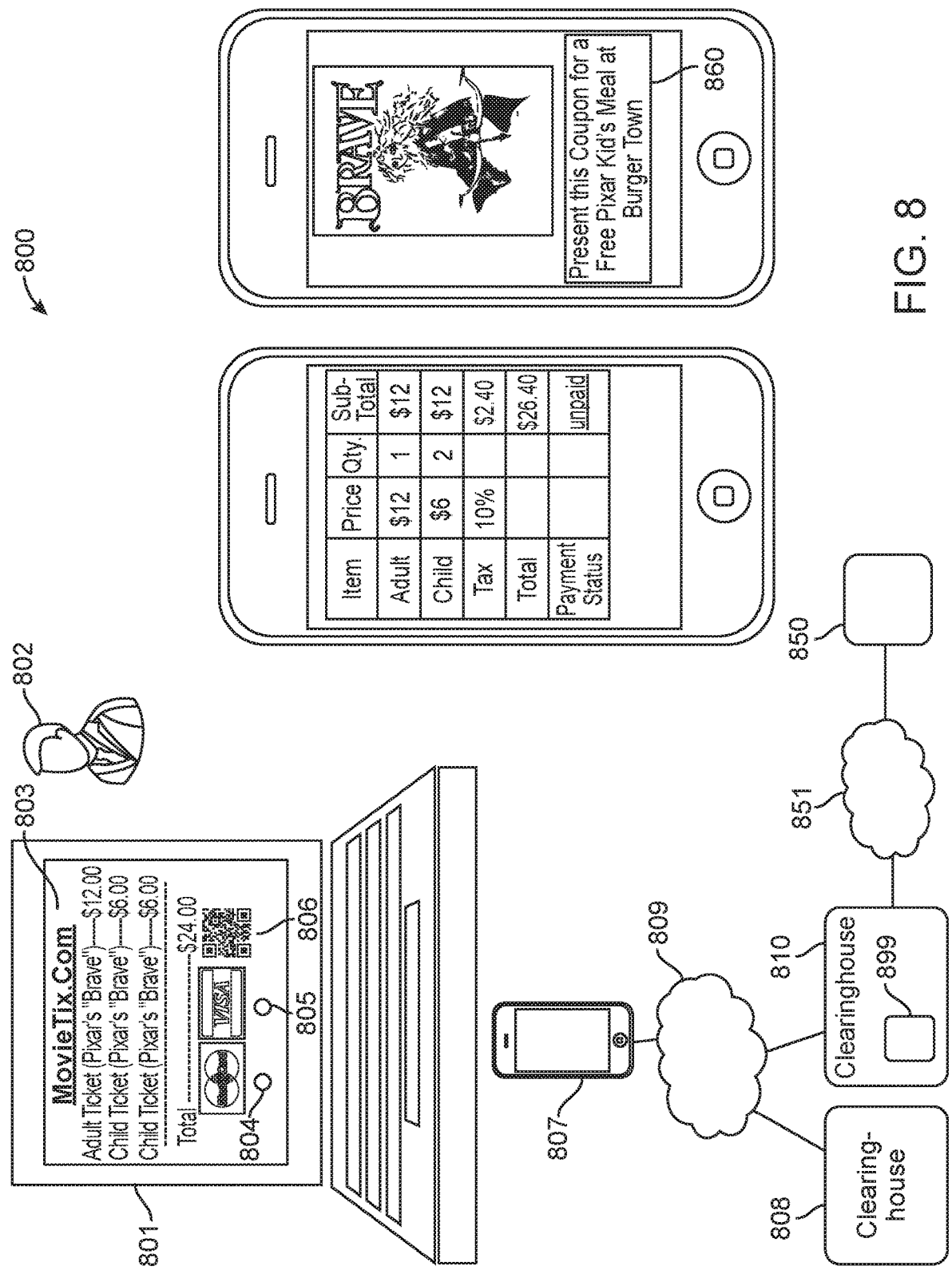
FIG. 8 illustrates a system for performing secure, optical-based financial transactions and serving highly relevant promotional content according to some embodiments of the present technology.

FIG. 8 illustrates a system 800 for performing secure, optical-based financial transactions and serving highly relevant promotional content according to some embodiments of the present technology. As shown, the system 800 includes a user computer 801 connected to the internet. Also shown, a user 802 finds items online that he would like to purchase. Upon checking out of an online store 803, the user is presented with credit card payment options 804, 805 as well as a more secure payment option in the form of an optical code 806.

The online store 803 has a verified account with a clearinghouse 808 such that when a user 802 scans the optical code 806 using a camera on a network-connected device 807, the clearinghouse 808 sends the user payment information via one or more network 809 to the network-connected device 807. In some embodiments, the user already has a verified account with a clearinghouse 810 in which the clearinghouse 810 stores the user's payment information. Clearinghouses 810 can be the same or different entities. Next, the user 802 reconciles the payment using the network-connected device 807 by authorizing the clearinghouse 810 to make the payment without ever providing the online store 803 with sensitive financial information.

Also, in some embodiments of the present technology, the clearinghouse 810 contains a user profile 899 with user information such as shipping address and user purchase data relating to the user's purchases. For example, in the illustrated example, the user profile stores information relating to the fact that the user 802 purchased a child's ticket to Pixar movie.

As explained above, some embodiments of the present technology involve serving highly relevant promotional content. Indeed, in some embodiments of the present technology, the clearinghouse 810 is connected to a promotional content delivery server 850 via a network 851. Networks 809 and 851 can comprise the same or different networks. The promotional content delivery server 850 is configured to access user data from the clearinghouse 810 and is configured to select promotional content to deliver to the user by analyzing the user profile and past purchase data. For example, according to FIG. 8, the clearinghouse 810 shares the fact that the user bought a child's ticket to a Pixar movie with the promotional content delivery server 850. Using this information, the promotional content delivery server 850 is able to serve the user with a sales promotion 860 that is highly relevant to parents having children that enjoy Pixar movies. Indeed, such a highly relevant promotion could demand a very high cost per impression.

As described herein, one aspect of the present technology is the gathering and use of data available from various sources to improve the delivery of invitational content including, promotions, advertisements, or any other content that may be of interest to users. The present disclosure contemplates that, in some instances, this gathered data may include personal information data that uniquely identifies or can be used to contact or locate a specific person. Such personal information data can include demographic data, location-based data, telephone numbers, email addresses, twitter ID's, home addresses, or any other identifying information.

The present disclosure recognizes that the use of such personal information data in the present technology can be used to the benefit of users. For example, the personal information data can be used to better understand user behavior, facilitate and measure the effectiveness of advertisements, applications, and delivered content. Accordingly, use of such personal information data enables calculated control of the delivered content. For example, the system can reduce the number of times a user receives a given ad or other content and can thereby select and deliver content that is more meaningful to users. Such changes in system behavior improve the user experience. Further, other uses for personal information data that benefit the user are also contemplated by the present disclosure.

The present disclosure further contemplates that the entities responsible for the collection, analysis, disclosure, transfer, storage, or other use of such personal information data should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after the informed consent of the users. Additionally, such entities would take any needed steps for safeguarding and securing access to such personal information data and ensuring that others with access to the personal information data adhere to their privacy and security policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for advertisement delivery services. In yet another example, users can configure their devices or user terminals to prevent storage or use of cookies and other mechanisms from which personal information data can be discerned.

The present disclosure also contemplates that other methods or technologies may exist for blocking access to their personal information data.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

Besides point-of-sale transactions, the utility of the present technology can be extended to many scenarios involving the transfer of sensitive information. For example, in some embodiments of the present technology, a driver's license, social security card, birth certificate, immunization record, visa, etc. can be stored in connection with a claim number that is encoded as an optical code and retrieved from the cloud on demand.

In another example, the present technology can be extended to the medical field. Prescription transcription errors are extremely dangerous and can be made very easily. Also, patients may be embarrassed or be subject to discrimination if another person happens to see the contents of a paper prescription that the patient possesses. Consequently, the present technology provides solutions for doctors writing prescriptions, patients delivering them, and pharmacists dispensing medicine.

Figure 9:
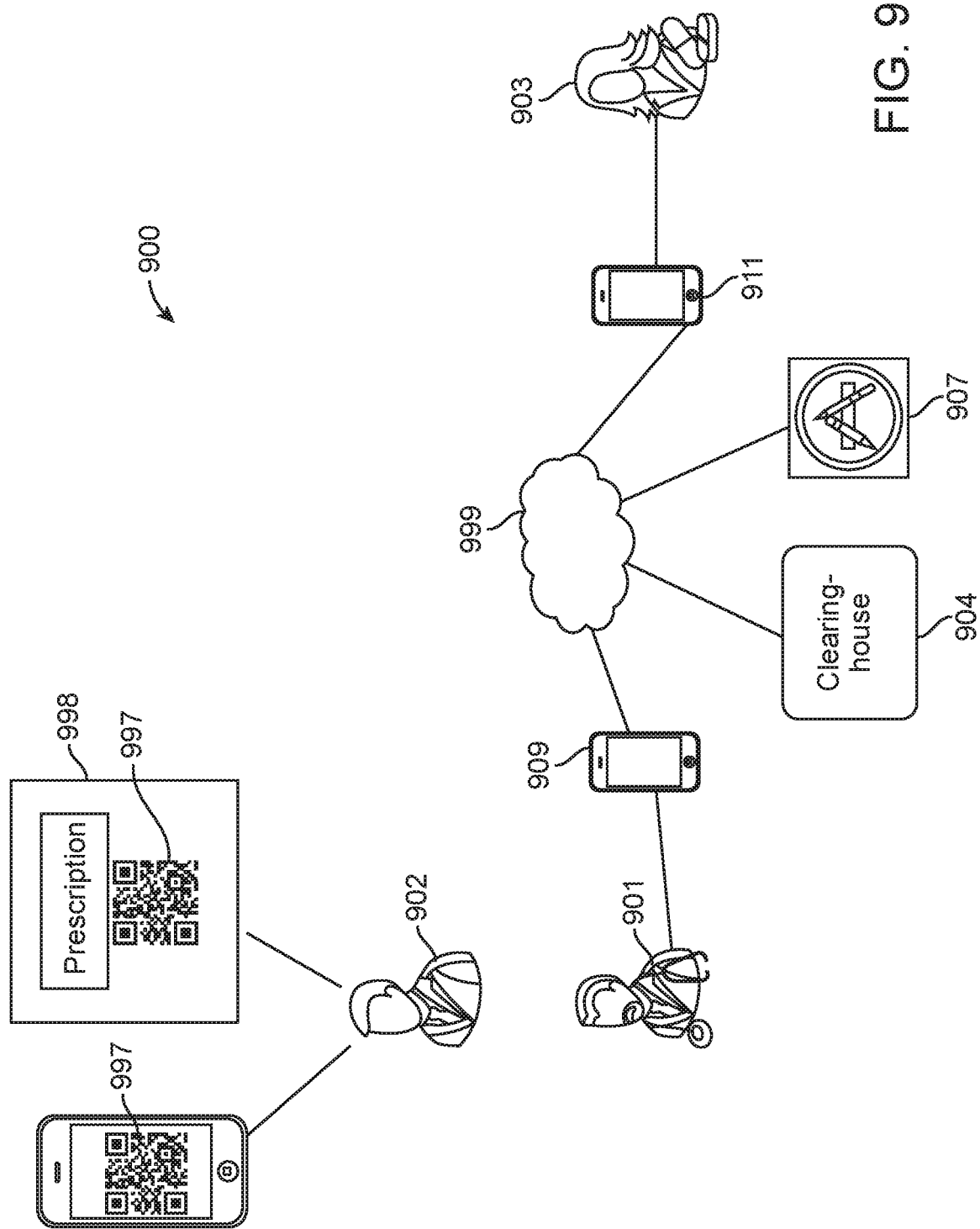
FIG. 9 illustrates an exemplary system for a prescription medicine lifecycle management using optical coupling according to some embodiments of the present technology.

FIG. 9 illustrates an exemplary system 900 for a prescription medicine lifecycle management system that benefits from optical coupling according to some embodiments of the present technology.

The system 900 of FIG. 9 is configured for enabling doctors 901, patients 902, and pharmacists 903 to complete a prescription fulfillment lifecycle using an optical code, a plurality of devices 909, 911 equipped with a camera and a code reading application, and one or more clearinghouses 904 available via one or more networks 999. According to the system 900 if FIG. 9, a doctor 901 diagnoses a patient 902 and prescribes medicine. A traditional prescription, that is prone to transcription error, can be avoided by the doctor using a computer device 909 coupled with a clearinghouse and software for encoding a claim number as an optical code and associating the optical code with the prescription. In some embodiments of the present technology, the doctor must first create a verified account with a clearinghouse 904. In some embodiments of the present technology, the doctor interacts with the clearinghouse 904 via a browser-based interface. However, in some other embodiments, the doctor interfaces with the clearinghouse 904 via a stand-alone, dedicated application. In some embodiments of the technology, such an application resides on, and is available for download from a network-based application platform 907, such as AppStore.sup.SM, available from Apple Inc. of Cupertino, Calif.

Once the doctor 901 has a verified account, the doctor 901 can upload prescription data to one or more cloud-based server along with a claim number that is recognizable by the clearinghouse 904. The clearinghouse 904 associates the prescription with a claim number and encodes the claim number as an optical code, thereby concealing the contents thereof and the clearinghouse 904 sends the optical code back to the doctor 901.

Next, the doctor 901 presents the prescription 998 embodied within an optical code 997, to the patient 902—either in printed form or on a display device. The patient 902 can now bring the encoded claim number to his pharmacist 903 to be decoded and the prescription filled. The pharmacist 903 also has a device 911 equipped with a camera and an optical code reader. Accordingly, the pharmacist 903 can use her device to decode the optical code 997, access the prescription from the cloud, and read the prescription from the printed form 912 or on the patient's device 913. When the pharmacist 903 scans and decodes the optical code 997, the clearinghouse delivers the information to the pharmacist, and she is shown the contents of the prescription and any accompanying doctor notes associated therewith. Patient privacy can be enhanced because the doctor does not necessarily need to know which pharmacy was used to fill the prescription—whether it is a neighborhood pharmacy or a licensed pharmacy in another state or country Likewise, the pharmacy does not necessarily need to know which doctor has been making the prescriptions. Both the doctor and the pharmacist can trust the assurance of the cloud that the other professional has been verified to have the appropriate credentials and legal requirements. The patient can get the prescription from any legitimate source after considerations such as convenience and price.

In some embodiments, the clearinghouse is connected with a user profile database or an insurance database. In these embodiments, the encoded claim number is associated with prescription information that can include a user data, such as insurance data, a co-pay amount, etc.

In some embodiments, a prescription linked with an encoded claim number indicates a number of refills available for a particular medicine. In these embodiments, the pharmacist 903 can communicate back to the clearinghouse 904 that a prescription has been fulfilled and the clearinghouse deducts one refill from the total remaining refills. In some embodiments of the present technology, the clearinghouse 904 comprises or is part of a central prescription-tracking network that tracks all filled prescriptions. Consequently, a patient cannot visit a second doctor in attempt to get a second prescription for the same medication, thereby inhibiting prescription drug abuse.

Also in the medical field, it is oftentimes desirable to have medical information on hand. For example, many individuals carry a card that conveys emergency contact information, blood type, medical allergies, organ donation information, etc. Additionally, many individuals live with medical conditions that require them to carry explicit instructions for conveying life-saving information to first responders in the event of a foreseeable medical emergency. However, as society moves toward paperless records and electronic wallets, hard copies of medical information may become less common. Therefore, solutions are required for carrying medical information in a secure, private fashion. Accordingly, some embodiments of the present technology involve associating medical information with a claim number encoded as an optical code.

Some embodiments of the present technology involve associating medical information with a claim number encoded as an optical code and providing a way for medical professionals and first responders to access the information easily. More specifically, some embodiments of the present technology involve displaying an encoded claim number that is associated with the individual's medical information in a user interface on a mobile device. In the event of an emergency or other medical situation, a medical professional can decode the optical code using a code reader and access the necessary patient records.

However, mobile devices frequently have password locks that would prevent emergency responders from accessing the emergency contact information and other relevant medical information that may be present on a device. Therefore, in some embodiments of the invention, a mobile device is configured such that a locked device still displays an optical code directly on the locked screen or via a screen reachable even when locked. In some other embodiments, an optical code may be painted or etched at manufacturing time to the body of a mobile device. In some embodiments, the code is associated with a secure access controlled document that resides on a cloud. According to these embodiments, an emergency responder may use their own camera phone to scan the code from the locked device screen or body of someone who is incapacitated and the software on the responder's phone would send a claim for the document linked with the optical code number to the cloud. In some embodiments, the cloud then verifies the credentials of the emergency responder, who already has a pre-verified account on the cloud, and securely sends back the corresponding document which may include emergency contact information, medical history, current medication, drug allergies etc.

Figure 10:
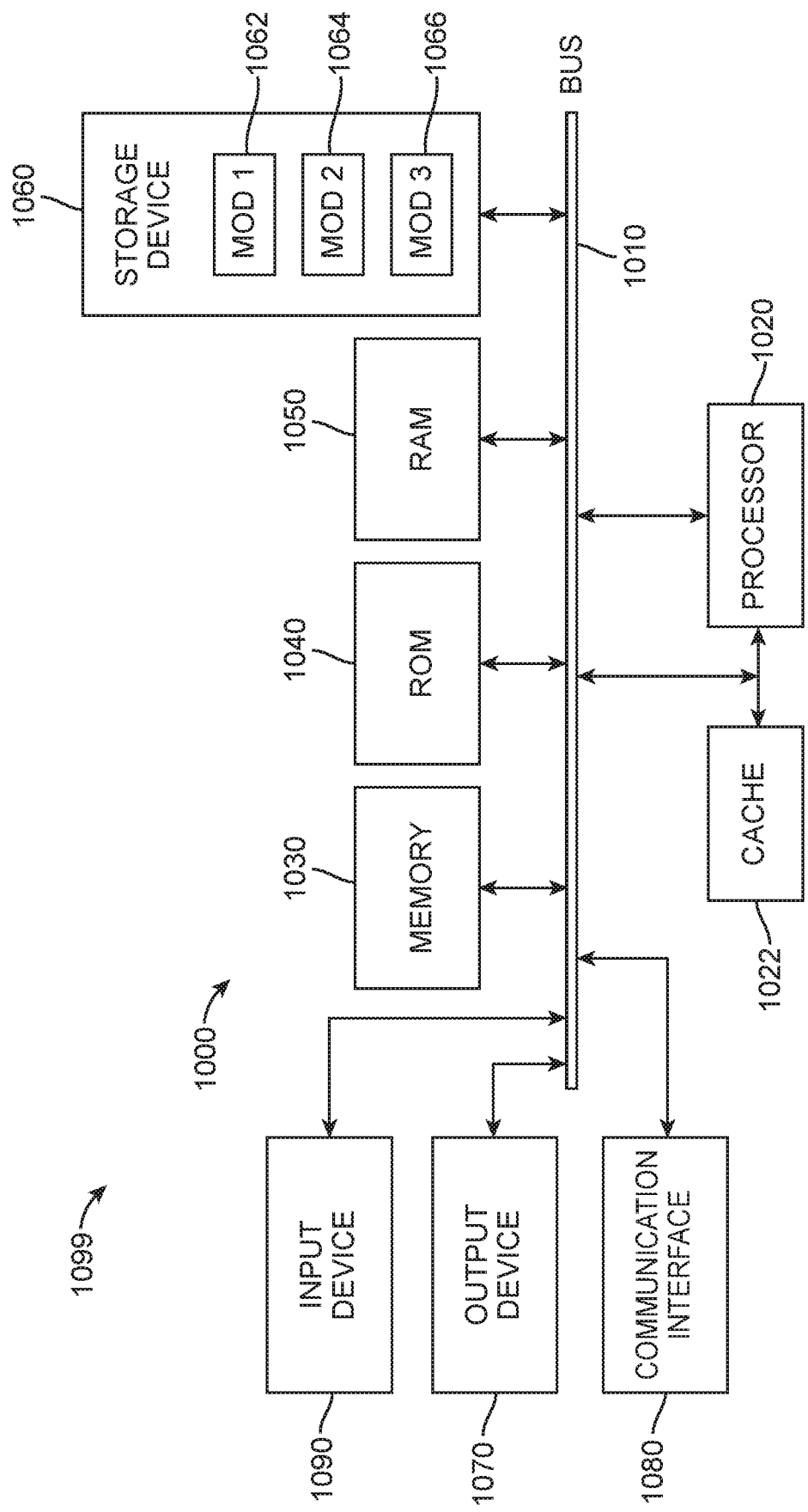
FIG. 10 illustrates an exemplary computer system according to some embodiments of the present technology.

The systems and methods disclosed broadly herein are configured to be implemented on one or more computer systems. FIG. 10 illustrates an exemplary computer system 1099 for implemented the present technology according to some embodiments of the present technology. According to FIG. 10, the computer system 1099 includes a general-purpose computing device 1000, including a processing unit (CPU or processor) 1020 and a system bus 1010 that couples various system components including the system memory 1030 such as read only memory (ROM) 1040 and random access memory (RAM) 1050 to the processor 1020. The system 1000 can include a cache 1022 of high speed memory connected directly with, in close proximity to, or integrated as part of the processor 1020. The system 1000 copies data from the memory 1030 and/or the storage device 1060 to the cache 1022 for quick access by the processor 1020. In this way, the cache provides a performance boost that avoids processor 1020 delays while waiting for data.

These and other modules can control or be configured to control the processor 1020 to perform various actions. Other system memory 1030 may be available for use as well. The memory 1030 can include multiple different types of memory with different performance characteristics. It can be appreciated that the disclosure may operate on a computing device 1000 with more than one processor 1020 or on a group or cluster of computing devices networked together to provide greater processing capability. The processor 1020 can include any general purpose processor and a hardware module or software module, such as module 1 1062, module 2 1064, and module 3 1066 stored in storage device 1060, configured to control the processor 1020 as well as a special-purpose processor where software instructions are incorporated into the actual processor design. The processor 1020 may essentially be a completely self-contained computing system, containing multiple cores or processors, a bus, memory controller, cache, etc. A multi-core processor may be symmetric or asymmetric.

The system bus 1010 may be any of several types of bus structures including a memory bus or memory controller, a peripheral bus, and a local bus using any of a variety of bus architectures. A basic input/output (BIOS) stored in ROM 1040 or the like, may provide the basic routine that helps to transfer information between elements within the computing device 1000, such as during start-up. The computing device 1000 further includes storage devices 1060 such as a hard disk drive, a magnetic disk drive, an optical disk drive, tape drive or the like. The storage device 1060 can include software modules 1062, 1064, 1066 for controlling the processor 1020. Other hardware or software modules are contemplated. The storage device 1060 is connected to the system bus 1010 by a drive interface. The drives and the associated computer readable storage media provide non-volatile storage of computer readable instructions, data structures, program modules and other data for the computing device 1000. In one aspect, a hardware module that performs a particular function includes the software component stored in a non-transitory computer-readable medium in connection with the necessary hardware components, such as the processor 1020, bus 1010, display 1070, and so forth, to carry out the function. The basic components are known to those of skill in the art and appropriate variations are contemplated depending on the type of device, such as whether the device 1000 is a small, handheld computing device, a desktop computer, or a computer server.

Although the exemplary embodiment described herein employs the hard disk 1060, it should be appreciated by those skilled in the art that other types of computer readable media which can store data that are accessible by a computer, such as magnetic cassettes, flash memory cards, digital versatile disks, cartridges, random access memories (RAMs) 1050, read only memory (ROM) 1040, a cable or wireless signal containing a bit stream and the like, may also be used in the exemplary operating environment. Non-transitory computer-readable storage media expressly exclude media such as energy, carrier signals, electromagnetic waves, and signals per se.

To enable user interaction with the computing device 1000, an input device 1090 represents any number of input mechanisms, such as a microphone for speech, a touch-sensitive screen for gesture or graphical input, keyboard, mouse, motion input, speech and so forth. An output device 1070 can also be one or more of a number of output mechanisms known to those of skill in the art. In some instances, multimodal systems enable a user to provide multiple types of input to communicate with the computing device 1000. The communications interface 1080 generally governs and manages the user input and system output. There is no restriction on operating on any particular hardware arrangement and therefore the basic features here may easily be substituted for improved hardware or firmware arrangements as they are developed.

For clarity of explanation, the illustrative system embodiment is presented as including individual functional blocks including functional blocks labeled as a "processor" or processor 1020. The functions these blocks represent may be provided through the use of either shared or dedicated hardware, including, but not limited to, hardware capable of executing software and hardware, such as a processor 1020, that is purpose-built to operate as an equivalent to software executing on a general purpose processor. For example, the functions of one or more processors presented in FIG. 10 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 1040 for storing software performing the operations discussed below, and random access memory (RAM) 1050 for storing results. Very large scale integration (VLSI) hardware embodiments, as well as custom VLSI circuitry in combination with a general purpose DSP circuit, may also be provided.

The logical operations of the various embodiments are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. The system 1000 shown in FIG. 10 can practice all or part of the recited methods, can be a part of the recited systems, and/or can operate according to instructions in the recited non-transitory computer-readable storage media. Such logical operations can be implemented as modules configured to control the processor 1020 to perform particular functions according to the programming of the module. For example, FIG. 10 illustrates three modules Mod1 1062, Mod2 1064 and Mod3 1066 which are modules configured to control the processor 1020. These modules may be stored on the storage device 1060 and loaded into RAM 1050 or memory 1030 at runtime or may be stored as would be known in the art in other computer-readable memory locations.

What is claimed is:

1. A computer-implemented method comprising:
    receiving, at a server of a prescription clearinghouse system, a first data file corresponding to a prescription, wherein the first data file includes a patient identifier associated with the prescription;
    generating, via the server, a database entry in a database of the prescription clearinghouse system associating a unique claim number with the first data file and a prescription fulfillment status indicating non-fulfillment;
    transmitting, by the server to a mobile client device associated with the patient identifier, a second data file including an optical code encoding the unique claim number;
    receiving, from a pharmacy system registered with the server, a request for access to the prescription associated with the optical code captured by the pharmacy system, the request including the unique claim number;
    transmitting, by the server to the pharmacy system in response to the request, the prescription associated with the unique claim number, the prescription having the patient identity and the doctor identity anonymized;
    reconciling payment for the prescription and sending confirmation of payment to the pharmacy system;
    receiving, at the server from the pharmacy system, a confirmation message indicating that the prescription was processed by the pharmacy system; and
    updating, via the server, the prescription fulfillment status in the database for the unique claim number based on the confirmation message.

2. The method of claim 1, wherein the first data file includes additional instructions from a medical professional.

3. The method of claim 1, wherein the first data file includes re-fill information relating to a frequency and a number of refills for the prescription, and wherein the prescription fulfillment status indicates a number of refills remaining for the prescription.

4. The method of claim 3, the updating further comprising adjusting the number of refills remaining based on the confirmation message.

5. The method of claim 1, further comprising:
    obtaining, by the server, prescription insurance information associated with the patient identifier; and
    associating the prescription insurance information with the database entry, and wherein the prescription insurance information is encoded into the optical code.

6. The method of claim 1, further comprising:
    transmitting, by the server to a prescription entry system corresponding to the doctor identity, a notification message that the prescription was processed in response to receiving the confirmation message.

7. A system comprising: a processor; and
    a computer-readable medium having stored thereon a plurality of code sections for causing the processor to perform operations comprising:
    obtaining, from a prescription entry system associated with a prescription clearinghouse system, a first data file corresponding to a prescription, wherein the first data file includes a patient identifier associated with the prescription;
    generating, in a database associated with the clearinghouse system, a database entry associating a unique claim number with the first data file and a prescription fulfillment status indicating non-fulfillment;
    transmitting, to a mobile client device associated with the patient identifier, a second data file including an optical code encoding the unique claim number;
    receiving, from a pharmacy system, a request for access to the prescription associated with the optical code captured by the pharmacy system, the request including the unique claim number;
    transmitting, to the pharmacy system in response to the request the prescription associated with the unique claim number, the prescription having the patient identity and the doctor identity anonymized;
    reconciling payment for the prescription and sending confirmation of payment to the pharmacy system;
    receiving, from the pharmacy system, a confirmation message indicating that the prescription was processed by the pharmacy system; and
    updating, in the database, the prescription fulfillment status for the unique claim number based on the confirmation message.

8. The system of claim 7, wherein the first data file includes additional instructions from a medical professional.

9. The system of claim 7, wherein the first data file includes re-fill information relating to a frequency and a number of refills for the prescription, and wherein the prescription fulfillment status indicates a number of refills remaining for the prescription.

10. The system of claim 9, the updating further comprising adjusting the number of refills remaining based on the confirmation message.

11. The system of claim 7, the plurality of code sections further configured for causing the processor to perform operations comprising:
    obtaining prescription insurance information associated with the patient identifier; and
    associating the prescription insurance information with the database entry, and wherein the prescription insurance information is encoded into the optical code.

12. The system of claim 7, the plurality of code sections further configured for causing the processor to perform operations comprising:
    transmitting, to the prescription entry system corresponding to the doctor identity, a notification message that the prescription was processed in response to receiving the confirmation message.

13. A non-transitory computer-readable medium having stored thereon a computer program executable by a computing device, the computer program comprising a plurality of code sections for:
    obtaining, from a prescription entry system registered with a clearinghouse system, a first data file corresponding to a prescription, wherein the first data file includes a patient identifier associated with the prescription;
    generating, in a database associated with the clearinghouse system, a new database entry associating a unique claim number with the first data file and a prescription fulfillment status indicating non-fulfillment;
    transmitting, to a mobile client device associated with the patient identifier, a second data file including an optical code encoding the unique claim number;
    receiving, from a pharmacy system registered with the clearinghouse system, a request for access to the prescription associated with the optical code captured by the pharmacy system, the request including the unique claim number;
    transmitting, to the pharmacy system in response to the request, the prescription associated with the unique claim number, the prescription having the patient identity and the doctor identity anonymized;
    reconciling payment for the prescription and sending confirmation of payment to the pharmacy system;
    receiving, from the pharmacy system, a confirmation message indicating that the prescription was processed by the pharmacy system; and
    updating, in the database, the prescription fulfillment status for the unique claim number based on the confirmation message.

14. The non-transitory computer-readable medium of claim 13, wherein the first data file includes additional instructions from a medical professional.

15. The non-transitory computer-readable medium of claim 13, wherein the first data file includes re-fill information relating to a frequency and a number of refills for the prescription, and wherein the prescription fulfillment status indicates a number of refills remaining for the prescription.

16. The non-transitory computer-readable medium of claim 15, the updating further comprising adjusting the number of refills remaining based on the confirmation message.

17. The non-transitory computer-readable medium of claim 13, further comprising:
    obtaining prescription insurance information associated with the patient identifier; and
    associating the prescription insurance information with the database entry, and wherein the prescription insurance information is encoded into the optical code.

18. The non-transitory computer-readable medium of claim 13, further comprising:
    transmitting, to the prescription entry system corresponding to the doctor identity, a notification message that the prescription was processed in response to receiving the confirmation message.

* * * * *